US012616600B2

(12) United States Patent
       Kang

(10) Patent No.:    US 12,616,600 B2
(45) Date of Patent:        May 5, 2026

(54) UPPER LIMB STABILIZING APPARATUS

(71) Applicant: SAMSUNG LIFE PUBLIC WELFARE FOUNDATION, Seoul (KR)

(72) Inventor: Seungtak Kang, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 57 days.

(21) Appl. No.: 18/706,422

(22) PCT Filed: Nov. 15, 2022

(86) PCT No.: PCT/KR2022/017947
       § 371 (c)(1),
       (2) Date: May 1, 2024

(87) PCT Pub. No.: WO2023/085896
       PCT Pub. Date: May 19, 2023

(65) Prior Publication Data
       US 2024/0407940 A1      Dec. 12, 2024

(30) Foreign Application Priority Data

Nov. 15, 2021    (KR) ........................ 10-2021-0156927

(51) Int. Cl.
       *A61F 5/37*         (2006.01)
       *A61F 5/058*       (2006.01)
(52) U.S. Cl.
       CPC ........ *A61F 5/3776* (2013.01); *A61F 5/05858* (2013.01)

(58) Field of Classification Search
       CPC .... A61F 5/0118; A61F 5/013; A61F 5/05866; A61F 5/058; A61F 5/05858; A61F 5/37; A61F 5/3776; A61F 5/3792
       See application file for complete search history.

(56) References Cited

U.S. PATENT DOCUMENTS 3,678,926 A  *  7/1972  Strittmatter ......... A61F 5/05858
                                                        602/21
3,815,588 A      6/1974  Klausner
                        (Continued)

FOREIGN PATENT DOCUMENTS

EP          0 776 184 B1      4/1998
KR     10-0817531 B1      3/2008
                        (Continued)

OTHER PUBLICATIONS

International Search Report & Written Opinion issued Feb. 22, 2023 in PCT/KR2022/017947, filed on Nov. 15, 2022, 13 pages (with English Translation).
                        (Continued)

*Primary Examiner* — Ophelia A Hawthorne
(74) *Attorney, Agent, or Firm* — Oblon, McClelland, Maier & Neustadt, L.L.P.

(57)                    ABSTRACT
A stabilizing apparatus includes a Velcro portion arranged at an arm-fixing portion and a hand-fixing portion to attach or detach an arm-fixing portion and the arm-resting portion, and the hand-fixing portion and the hand-resting portion, respectively, to or from each other. Through this, the present disclosure maintains a supination posture of a forearm of an upper limb paralysis patient on a lab board, and the present disclosure deforms a wrist and fingers to a flexion posture instead of an extended posture when attaching Velcro.

9 Claims, 7 Drawing Sheets

(56)                References Cited

U.S. PATENT DOCUMENTS

| | | | | |
|---|---|---|---|---|
| 4,316,454 | A | | 2/1982 | Perka |
| 5,069,203 | A | * | 12/1991 | Anderson ............ A61F 13/108 |
| | | | | 602/21 |
| 5,772,620 | A | | 6/1998 | Szlema et al. |
| 6,945,252 | B2 | | 9/2005 | Mengato |
| 2005/0145255 | A1 | * | 7/2005 | Mengato ............ A61F 5/05866 |
| | | | | 128/878 |
| 2018/0104125 | A1 | * | 4/2018 | Vahala ................... A61G 7/075 |
| 2020/0030047 | A1 | * | 1/2020 | Gordon ................. A61B 46/27 |

FOREIGN PATENT DOCUMENTS

| | | | |
|---|---|---|---|
| KR | 10-2016-0134336 | A | 11/2016 |
| KR | 10-1978075 | B1 | 5/2019 |
| KR | 10-2021-0040995 | A | 4/2021 |
| KR | 10-2021-0065784 | A | 6/2021 |

OTHER PUBLICATIONS

Korean Office Action issued Nov. 26, 2023 in KR Application 10-2021-0156927, filed on Nov. 15, 2021, 10 pages.
Korean Written Decision on Registration issued Nov. 20, 2023 in KR application 10-2021-0156927, filed on Nov. 15, 2021, 5 pages.
Extended European Search Report issued Oct. 15, 2025, in corresponding European Patent Application No. 22893315.6, 6 pages.

* cited by examiner

UPPER LIMB STABILIZING APPARATUS

TECHNICAL FIELD

Embodiments of the present disclosure relate to an upper limb stabilizing apparatus.

BACKGROUND ART

When a patient with upper limb (arm) paralysis uses a wheelchair, a lab board is generally mounted on the wheelchair to be used. Here, the arm paralysis patient using the lab board lives with the paralyzed arm in a forearm pronation posture.

Muscle tension of the paralyzed arm is increased and over time, the paralyzed arm is deformed to the pronation posture and joint contracture occurs. The pronation posture on the lab board may be a posture that promotes such a negative deformation. Accordingly, it is necessary to encourage the arm paralysis patient to change a posture of placing the arm on the lab board from the pronation posture to a supination posture that is a posture opposite to the pronation posture.

Also, in an arm paralysis patient, deformation or contracture occurs in a flexion posture, and when the pronation posture of the arm paralysis patient is maintained, this induces deformation or contracture.

DISCLOSURE

Technical Problem

In order to solve above-described problems, the present disclosure provides an upper limb stabilizing apparatus assisting an upper limb paralysis patient to live with the forearm maintaining a supination posture on a lab board.

However, such problems are examples and problems to be solved in the present disclosure are not limited thereto.

Technical Solution

An upper limb stabilizing apparatus according to an embodiment of the present disclosure includes: an arm resting portion where an arm is rested; an arm fixing portion where the rested arm is fixed; a hand resting portion connected to the arm resting portion and where a hand is rested; a hand fixing portion where the rested hand is fixed; and a Velcro portion arranged at the arm fixing portion and the hand fixing portion to attach or detach the arm fixing portion and the arm resting portion, and the hand fixing portion and the hand resting portion, respectively, to or from each other.

In the upper limb stabilizing apparatus according to an embodiment of the present disclosure, the arm resting portion may be formed of soft memory foam.

In the upper limb stabilizing apparatus according to an embodiment of the present disclosure, the arm resting portion may include a medial epicondyle resting portion and a styloid process resting portion, wherein sponginess of the medial epicondyle resting portion and the styloid process resting portion may be greater than sponginess of a remaining portion of the arm resting portion.

In the upper limb stabilizing apparatus according to an embodiment of the present disclosure, attached positions of the arm fixing portion and the arm resting portion, and the hand fixing portion and the hand resting portion may be adjusted through the Velcro portion.

In the upper limb stabilizing apparatus according to an embodiment of the present disclosure, the arm fixing portion and the hand fixing portion may be formed as a net.

In the upper limb stabilizing apparatus according to an embodiment of the present disclosure, the arm resting portion and the hand resting portion may be arranged to have a first angle.

In the upper limb stabilizing apparatus according to an embodiment of the present disclosure, the hand resting portion may be formed in a triangular prism shape and an angle between a ground surface and a triangular slope of the hand resting portion may form a second angle.

In the upper limb stabilizing apparatus according to an embodiment of the present disclosure, the hand fixing portion may include a protruding first fixing portion and a second fixing portion, wherein the first fixing portion and the second angle may be arranged to have a third angle therebetween.

In the upper limb stabilizing apparatus according to an embodiment of the present disclosure, the hand fixing portion may include a hole portion into which a thumb is inserted.

In the upper limb stabilizing apparatus according to an embodiment of the present disclosure, a double-sided adhesive tape may be attached to a rear portion of the arm resting portion.

Other aspects, features, and advantages other than those described above will become apparent from the detailed descriptions, claims and drawings for carrying out the following disclosure.

Advantageous Effects

An upper limb stabilizing apparatus according to an embodiment of the present disclosure maintains a supination posture of a forearm of an upper limb paralysis patient on a lab board, thereby preventing possibilities of occurrence of negative deformation and contracture of the forearm, which may occur when the forearm maintains a pronation posture.

Also, an upper limb stabilizing apparatus according to an embodiment of the present disclosure deforms a wrist and fingers to a flexion posture instead of an extended posture, thereby preventing possibilities of occurrence of negative deformation and contracture of the wrist and fingers, which may occur when the wrist and fingers maintain the extended posture.

Also, an upper limb stabilizing apparatus according to an embodiment of the present disclosure is formed in a structure that allows a patient to feel comfortable.

Also, an upper limb stabilizing apparatus according to an embodiment of the present disclosure is easily stored and managed through a Velcro structure, can be manufactured with an inexpensive material and thus has relatively low manufacturing costs, and is easily attached or detached and thus can be conveniently worn.

The effects of the present disclosure are not limited to those mentioned above, and other effects that are not mentioned may be clearly understood by one of ordinary skill in the art from the scope of claims.

MODE FOR INVENTION

Figure 1:
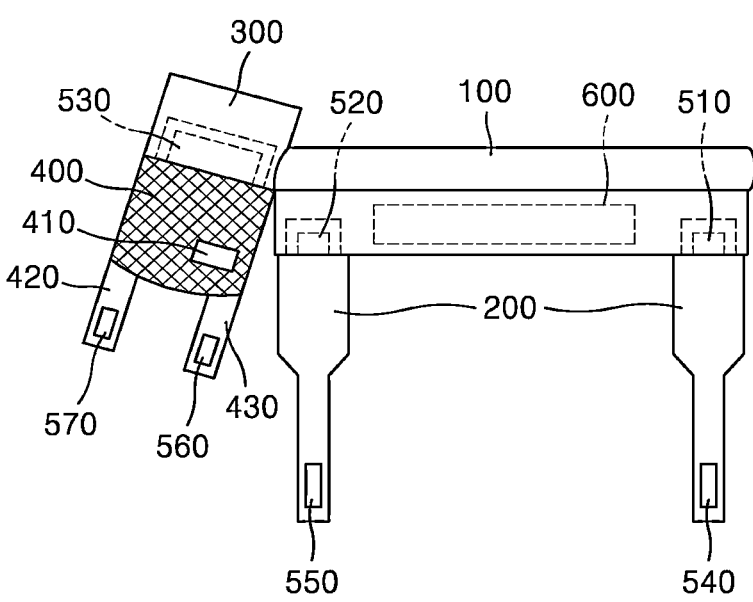
FIG. 1 is a diagram showing an upper limb stabilizing apparatus according to an embodiment of the present disclosure.

The present disclosure may have various modifications and various embodiments, and specific embodiments are illustrated in the drawings and are described in detail in the detailed description. However, this is not intended to limit the present disclosure to particular embodiments, and it will be understood that all changes, equivalents, and substitutes that do not depart from the spirit and technical scope of the present disclosure are encompassed in the present disclosure. While describing the present disclosure, same reference numerals are used for same components even if the components are illustrated in another embodiment.

Hereinafter, embodiments of the present disclosure will be described in detail with reference to the accompanying drawings, and in the following description with reference to the drawings, like reference numerals refer to like components and redundant descriptions thereof will be omitted.

In the following embodiments, the terms "first" and "second" are not used in a limited sense and are used to distinguish one component from another component.

In the following embodiments, an expression used in the singular encompasses the expression of the plural, unless it has a clearly different meaning in the context.

In the following embodiments, it will be further understood that the terms "comprise" and/or "comprising" used herein specify the presence of stated features or components, but do not preclude the presence or addition of one or more other features or components.

In the drawings, for convenience of description, sizes of components may be exaggerated or reduced. In other words, because sizes and thicknesses of components in the drawings are arbitrarily illustrated for convenience of explanation, the present disclosure is not necessarily limited thereto.

According to embodiments, an x-axis, a y-axis, and a z-axis are not limited to three axes on an orthogonal coordinate system, but may be interpreted in a broad sense including the three axes. For example, the x-axis, the y-axis, and the z-axis may be perpendicular to one another, or may represent different directions that are not perpendicular to one another.

When a certain embodiment may be implemented differently, a specific process order may be performed differently from the described order. For example, two consecutively described processes may be performed substantially at the same time or performed in an order opposite to the described order.

Also, the terms used in the present specification are only used to describe specific embodiments, and are not intended to limit the present disclosure. In the present specification, it is to be understood that terms such as "including" or "having", etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, an upper limb stabilizing apparatus according to an embodiment of the present disclosure will be described with reference to FIGS. 1, 2, 6, and 7.

Figure 2:
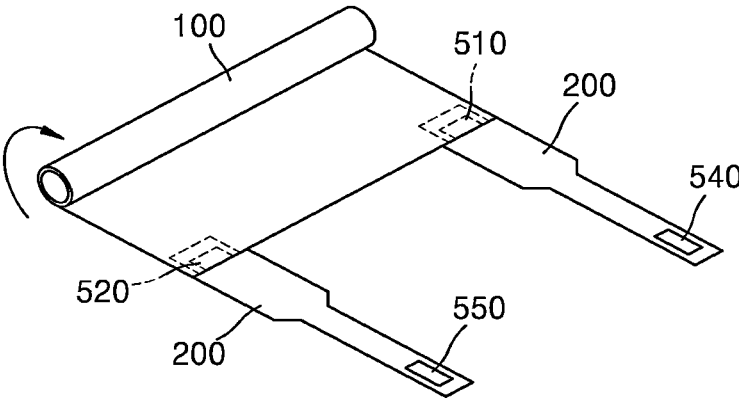
FIG. 2 is a diagram showing an arm resting portion of an upper limb stabilizing apparatus, according to an embodiment of the present disclosure.
Figure 6:
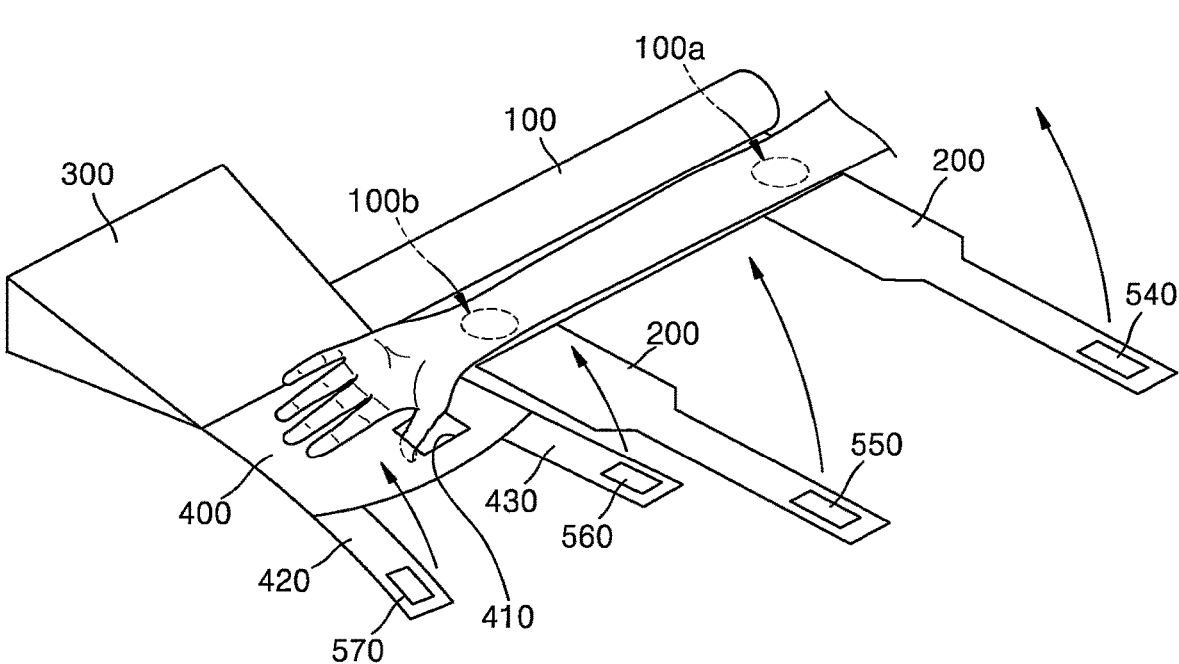
FIG. 6 is a diagram showing a structure in which a hand and arm of a patient are first rested in a pronation posture on an upper limb stabilizing apparatus.
Figure 7:
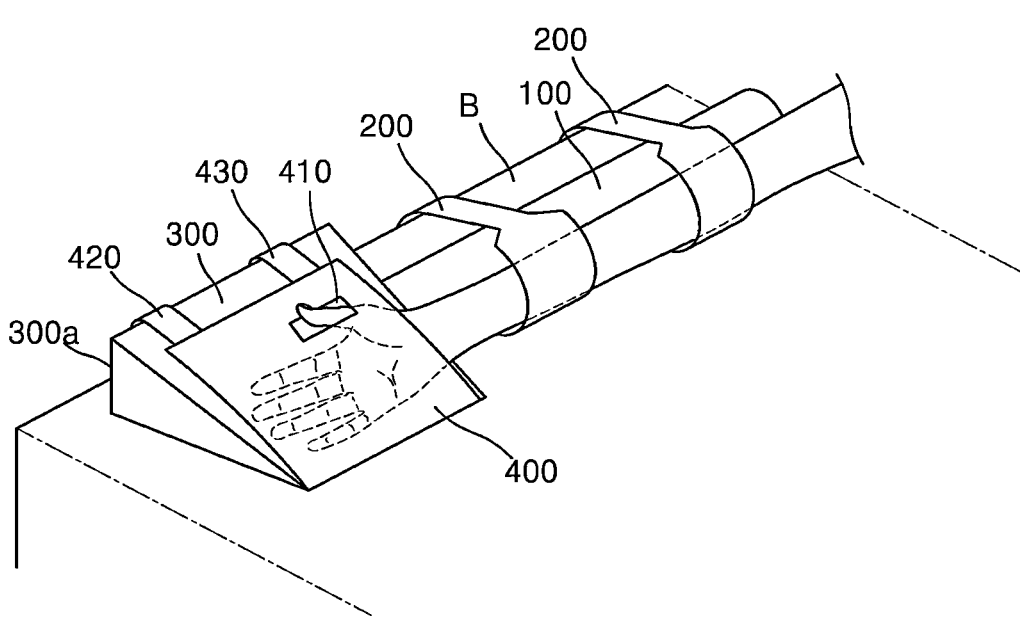
FIG. 7 is a diagram showing a structure, from that of FIG. 6, in which the upper limb stabilizing apparatus has fixed the hand and arm of the patient to a supination posture.

FIG. 1 is a diagram showing an upper limb stabilizing apparatus according to an embodiment of the present disclosure. FIG. 2 is a diagram showing an arm resting portion of the upper limb stabilizing apparatus, according to an embodiment of the present disclosure. FIG. 6 is a diagram showing a structure in which a hand and arm of a patient are first rested in a pronation posture on the upper limb stabilizing apparatus. FIG. 7 is a diagram showing a structure, from that of FIG. 6, in which the upper limb stabilizing apparatus has fixed the hand and arm of the patient to a supination posture.

Referring to FIGS. 1, 2, and 6, the upper limb stabilizing apparatus according to an embodiment of the present disclosure includes an arm resting portion 100 where an arm is rested, an arm fixing portion 200 where the rested arm is fixed, a hand resting portion 300 connected to the arm resting portion 100 and where a hand is rested, a hand fixing portion 400 where the rested hand is fixed, and a Velcro portion 500 arranged at the arm fixing portion 200 and the hand fixing portion 400 to attach or detach the arm fixing portion 200 and the arm resting portion 100, and the hand fixing portion 400 and the hand resting portion 300, respectively, to or from each other. As used herein. "Velcro" refers to a hook-and-loop fastener.

An outer forearm part may be rested in the arm resting portion 100. The arm resting portion 100 may be formed in a cylindrical shape. When the arm resting portion 100 is formed in the cylindrical shape, the arm rested in the arm resting portion 100 having the cylindrical shape maintains a supination posture of being supinated only by 45° instead of by 180° by a cylindrical surface, and thus, a patient maintains the supination posture, in which a hand is turned at a certain angle, so as to feel comfortable when the arm is fixed.

Also, the arm resting portion 100 is a portion where the arm is rested, and thus may be formed of a soft memory foam material. When the arm resting portion 100 is formed of a soft memory foam material, a bedsore and a wound, which may occur when the arm is fixed for a long period of time, may be prevented.

Referring to FIG. 1, a double-sided adhesive tape 600 may be attached to a rear surface of the arm resting portion 100. The upper limb stabilizing apparatus may fix the arm and hand of the patient while the upper limb stabilizing apparatus is fixed on a lab board through the double-sided adhesive tape 600. The double-sided adhesive tape 600 may be a reusable double-sided adhesive tape.

Referring to FIG. 6, the arm resting portion 100 includes a medial epicondyle resting portion 100*a* and a styloid process resting portion 100*b*, wherein sponginess of the medial epicondyle resting portion 100*a* and the styloid process resting portion 100b may be greater than sponginess of a remaining portion of the arm resting portion 100. The medial epicondyle resting portion 100a may correspond to an elbow part of the arm and the styloid process resting portion 100b may correspond to a wrist part.

Referring to FIG. 2, the arm fixing portion 200 may protrude from each of both ends of the arm resting portion 100. The arm fixing portions 200 may be attached to a lab board B to which the arm resting portion 100 is fixed, through Velcro portions 510 and 520. Here, the Velcro portions 510 and 520 may adjust attached positions to an attachment object, such as a lab board, thereby varying a fixing degree of the arm according to a condition of the patient's arm.

The protruding arm fixing portions 200 may fix the arm as the arm fixing portions 200 surround the arm rested in the arm resting portion 100 while Velcro portions 540 and 550 arranged at ends of the arm fixing portion 200 are attached and fixed to one surface portion of the arm resting portion 100.

Here, the Velcro portions 540 and 550 may adjust attached positions to the arm resting portion 100 thereby varying a fixing degree of the arm according to the condition of the arm, such as the size, fixing position, or the like of the patient's arm.

According to an embodiment of the present disclosure, the arm fixing portion 200 may be formed as a net. Accordingly, a breathable structure may be formed such that the patient's arm fixed through the arm fixing portion 200 is ventilated. Accordingly, a bedsore and a wound, which may occur in the patient's arm and hand due to long-term fixation, may be prevented.

Referring to FIG. 1, the hand fixing portion 400 may include first and second fixing portions 420 and 430. The first and second fixing portions 420 and 430 may respectively protrude from both ends of the hand fixing portion 400. The hand fixing portion 400 and the protruding first and second fixing portions 420 and 430 may fix the hand as the hand fixing portion 400 and the first and second fixing portions 420 and 430 surround the hand rested in the hand resting portion 300 while Velcro portions 560 and 570 arranged at ends of the first and second fixing portions 420 and 430 are attached and fixed to one surface portion of the hand resting portion 300. In detail, the Velcro portions 560 and 570 may be attached to a hand resting portion perpendicular surface portion 300a.

Here, the Velcro portions 560 and 570 may adjust attached positions to the hand resting portion 300 thereby varying a fixing degree of the hand according to a condition of the hand, such as the size, fixing position, or the like of the patient's hand.

The hand resting portion 300 is a portion where the hand is rested, and thus may be formed of a soft memory foam material. When the hand resting portion 300 is formed of a soft memory foam material, a bedsore and a wound, which may occur when the hand is fixed for a long period of time, may be prevented.

The hand fixing portion 400 may be attached to the hand resting portion 300 through a Velcro portion 530. Here, the Velcro portion 530 may adjust an attached position to the hand resting portion 300, thereby varying the fixing degree of the arm according to the condition of the patient's arm.

According to an embodiment of the present disclosure, the hand fixing portion 400 may be formed as a net. Accordingly, a breathable structure may be formed such that the patient's arm fixed through the hand fixing portion 400 is ventilated.

Referring to FIG. 7, a hole portion 410 may be formed in the hand fixing portion 400. The hole portion 410 may be arranged such that the hole portion 410 is formed at a location corresponding to the thumb of the hand so that, when the patient's arm and hand are fixed in an upside-down position, i.e., a supination posture, the thumb of the upside-down hand maintains being inserted into the hole portion 410.

Referring to FIGS. 6 and 7, first, the hand and the arm may be rested on the upper limb stabilizing apparatus of FIG. 6. Here, the hand and the arm may first be rested in a prone position, i.e., a pronation posture. While resting in the pronation posture, the thumb may be inserted into the hole portion 410.

After the hand and the arm are rested on the upper limb stabilizing apparatus, the arm fixing portion 200 and the hand fixing portion 400 are rolled up to be attached to the lab board B and the hand resting portion perpendicular surface portion 300a, as shown in FIG. 7, and at the same time, the hand and the arm rested in the pronation posture may be switched to the supination posture. Referring to FIG. 7, the arm fixing portion 200 may be attached to the lab board B and the first and second fixing portions 420 and 430 of the hand fixing portion 400 may be attached to the hand resting portion perpendicular surface portion 300a.

Hereinafter, first, second and third angles according to an embodiment of the present disclosure will be described with reference to FIGS. 3 to 5.

Figure 3:
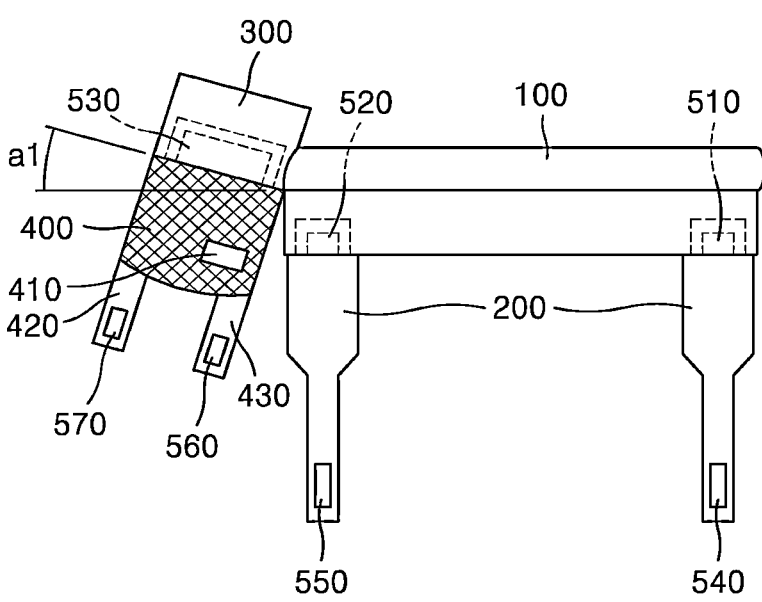
FIG. 3 is a diagram showing a first angle between a hand resting portion and an arm resting portion of an upper limb stabilizing apparatus, according to an embodiment of the present disclosure.

FIG. 3 is a diagram showing a first angle between a hand resting portion and an arm resting portion of an upper limb stabilizing apparatus, according to an embodiment of the present disclosure. FIG. 4 is a diagram showing a third angle between a first fixing portion and a third fixing portion of an upper limb stabilizing apparatus, according to an embodiment of the present disclosure. FIG. 5 is a diagram showing a second angle of an upper limb stabilizing apparatus, according to an embodiment of the present disclosure.

Referring to FIG. 3, the arm resting portion 100 and the hand resting portion 300 may be arranged to have a first angle a1. The hand and the arm are in a comfortable state if an angle therebetween is the first angle a1 when the hand and the arm maintain an upside-down state, and at the same time, changes and contractures in the arm and the joints of the hand may be prevented. According to the present embodiment, the first angle a1 may be 15 degrees.

The first angle a1 formed by the arm resting portion 100 and the hand resting portion 300 may be adjusted. The first angle a1 formed by the arm resting portion 100 and the hand resting portion 300 may be adjusted according to angles at which a user's hand and arm are rested and shapes of the user's arm and hand. For example, an angle between the arm resting portion 100 and the hand resting portion 300 may be adjusted to 0 degree, to 15 degrees according to an embodiment, or up to 30 degrees according to circumstances. Here, the angle may be adjusted by adjusting an attached angle of the hand resting portion 300 to the arm resting portion 100.

The hand resting portion 300 may be detached from the arm resting portion 100. When the patient uses a wrist prosthesis, the hand resting portion 300 may be removed from the arm resting portion 100 and then the arm may be fixed by using only the arm resting portion 100.

In addition, the hand fixing portion 400 may be detached from the hand resting portion 300. Accordingly, the patient's arm may be fixed by using only the hand resting portion 300 and the arm resting portion 100.

Figure 5:
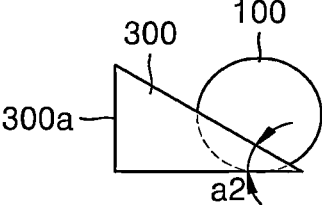
FIG. 5 is a diagram showing a second angle of an upper limb stabilizing apparatus, according to an embodiment of the present disclosure.

Referring to FIG. 5, the hand resting portion 300 may be formed in a triangular prism shape, and a ground surface and a triangular slope of the hand resting portion 300 may be formed to have a second angle a2. According to the present embodiment, the second angle a2 may be 45 degrees.

Accordingly, when the hand resting portion 300 is formed in the triangular prism shape, the hand rested on the hand resting portion 300 having the triangular prism shape is not completely supinated to the supination posture but maintains being supinated only by about 45 degrees by a triangular prism surface, and thus, the patient may feel comfortable with the fixed hand and arm compared to when the hand and arm are completely supinated.

The hand resting portion 300 is formed in the triangular prism shape and the arm resting portion 100 is formed in a cylindrical shape, and thus, a connecting portion of the hand resting portion 300 and the arm resting portion 100 may have a twisted shape.

Figure 4:
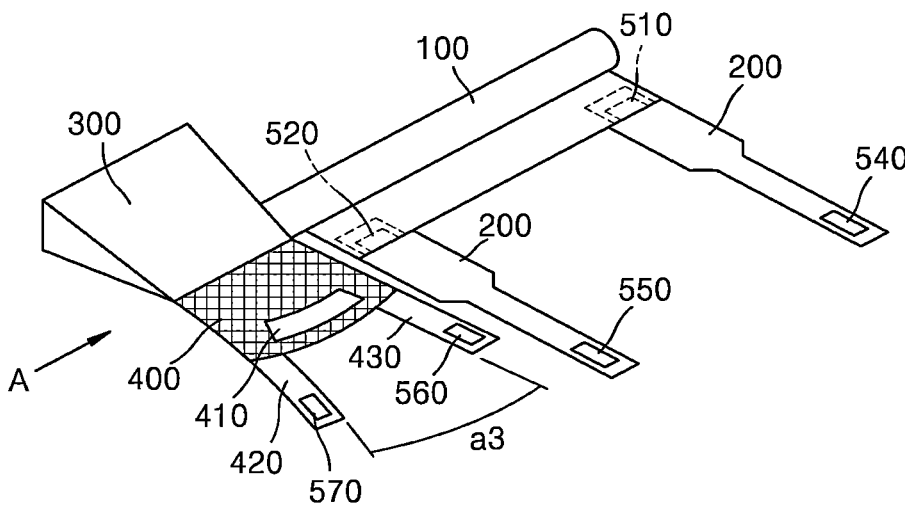
FIG. 4 is a diagram showing a third angle between a first fixing portion and a third fixing portion of an upper limb stabilizing apparatus, according to an embodiment of the present disclosure.

Referring to FIG. 4, the protruding first and second fixing portions 420 and 430 of the hand fixing portion 400 may be formed to have a third angle a3 therebetween. According to the present embodiment, the third angle a3 may be 30 degrees. Unlike the arm, the hand has a radial shape rather than an elongated shape, and thus, in order to fix the back of the hand and the five fingers, the first and second fixing portions 420 and 430 separated from each other at the third angle a3 may be provided. When the separated first and second fixing portions 420 and 430 are attached to the hand resting portion 300 while surrounding the hand, the first and second fixing portions 420 and 430 are attached while surrounding the hand in a spread state, and thus, the hand may be further stably fixed compared to when there is no angle.

The present disclosure has been described with reference to embodiments shown in the drawings, but the embodiments are merely examples. One of ordinary skill in the art may fully understand that other various modifications and equivalent embodiments are possible from the embodiments. Accordingly, the scope of the present disclosure will be defined based on the appended claims.

The specific technical content described in the embodiment is an example and does not limit the technical scope of the embodiment. In order to describe the disclosure concisely and clearly, descriptions of general technologies and configurations of the prior art may be omitted. In addition, connection or connection members of lines between components shown in the drawings exemplarily represent functional connections and/or physical or circuit connections, and in an actual apparatus, may be replaced or may be implemented as various additional functional connections, physical connections, or circuit connections. Also, components described herein may not be essential components for application of the present disclosure unless the components are particularly described as being "essential" or "critical".

The term "the" or similar referents described in the description and claims of the disclosure may refer to both the singular and the plural, unless otherwise specified. Further, when a range is described in an embodiment, the disclosure includes inventions to which individual values belonging to the range are applied (unless otherwise stated), and it is considered that each individual value configuring the range is described in the description of the disclosure. In addition, unless an order is clearly stated or unless otherwise stated, operations configuring a method according to an embodiment may be performed in an appropriate order. An embodiment is not necessarily limited by an order the operations are described.

In an embodiment, the use of all examples or exemplary terms (for example, "etc.") is merely for describing the embodiment in detail and the scope of the embodiment is not limited by those examples or exemplary terms unless defined in the claims. Also, it would be obvious to one of ordinary skill in the art that various modifications, combinations, and changes may be configured according to design conditions and factors within the scope of claims or equivalents.

The invention claimed is:

1. An upper-limb stabilizing apparatus, comprising:
an arm-resting portion configured to support an arm;
an arm-fixing portion configured to releasably secure the supported arm to the arm-resting portion;
a hand-resting portion connected to the arm-resting portion and where-a configured to support a hand;
a hand-fixing portion configured to releasably secure the hand to the hand-resting portion; and
a fastening portion disposed at the arm-fixing portion and the hand-fixing portion and comprising a hook-and-loop fastener, the fastening portion being configured to attach or detach the arm-fixing portion to the arm-resting portion and the hand-fixing portion to the hand-resting portion, respectively,
wherein the hand-fixing portion comprises a protruding first fixing portion and a second fixing portion, wherein the first fixing portion and the second fixing portion have a third angle therebetween.

2. The upper-limb stabilizing apparatus of claim 1, wherein the arm-resting portion is formed of soft memory foam.

3. The upper-limb stabilizing apparatus of claim 2, wherein the arm-resting portion comprises a medial epicondyle resting portion and a styloid process resting portion, and
wherein a sponginess of the medial epicondyle resting portion and the styloid process resting portion is greater than a sponginess of a remaining portion of the arm-resting portion.

4. The upper-limb stabilizing apparatus of claim 1, wherein attached positions of the arm-fixing portion and the arm-resting portion, and the hand-fixing portion and the hand-resting portion are adjusted through the hook-and-loop fastener.

5. The upper-limb stabilizing apparatus of claim 1, wherein the arm-fixing portion and the hand-fixing portion are formed as a net.

6. The upper-limb stabilizing apparatus of claim 1, wherein the arm-resting portion and the hand-resting portion are arranged to have a first angle therebetween.

7. The upper-limb stabilizing apparatus of claim 1, wherein the hand-resting portion is formed in a triangular prism shape and an angle between a ground surface and a triangular slope of the hand-resting portion forms a second angle.

8. The upper-limb stabilizing apparatus of claim 1, wherein the hand-fixing portion comprises a hole portion into which configured to receive a thumb is inserted.

9. The upper-limb stabilizing apparatus of claim 1, wherein a double-sided adhesive tape is attached to a rear portion of the arm-resting portion.

* * * * *